(12) United States Patent
Kloth et al.

(10) Patent No.: US 9,828,305 B2
(45) Date of Patent: *Nov. 28, 2017

(54) PROCESSES FOR THE PREPARATION OF AN OLEFINIC PRODUCT

(71) Applicant: SHELL OIL COMPANY, Houston, TX (US)

(72) Inventors: Antonius Gijsbertus Johannes Kloth, Vaals (NL); Sivakumar Sadasivan Vijayakumari, Gonzales, LA (US); Jeroen Van Westrenen, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/439,267

(22) PCT Filed: Oct. 29, 2013

(86) PCT No.: PCT/EP2013/072627
§ 371 (c)(1),
(2) Date: Apr. 29, 2015

(87) PCT Pub. No.: WO2014/067955
PCT Pub. Date: May 8, 2014

(65) Prior Publication Data
US 2015/0299067 A1 Oct. 22, 2015

(30) Foreign Application Priority Data
Oct. 31, 2012 (EP) .................................. 12190907

(51) Int. Cl.
*C07C 1/20* (2006.01)
*C10G 45/08* (2006.01)
*C10G 45/12* (2006.01)
*C10G 65/12* (2006.01)
*C07C 4/06* (2006.01)

(52) U.S. Cl.
CPC .................. *C07C 1/20* (2013.01); *C07C 4/06* (2013.01); *C10G 45/08* (2013.01); *C10G 45/12* (2013.01); *C10G 65/12* (2013.01); *C10G 2300/104* (2013.01); *C10G 2300/1011* (2013.01); *C10G 2300/1044* (2013.01); *C10G 2300/1051* (2013.01); *C10G 2300/1059* (2013.01); *C10G 2300/1081* (2013.01); *C10G 2300/1085* (2013.01); *C10G 2400/02* (2013.01); *C10G 2400/20* (2013.01); *C10G 2400/22* (2013.01); *Y02P 30/42* (2015.11)

(58) Field of Classification Search
CPC ................. C07C 1/00; C07C 1/20; C07C 4/06
USPC ....... 585/638, 639, 640, 641, 648, 800, 809, 585/330, 300, 301, 310; 62/121
See application file for complete search history.

(56) References Cited

U.S. PATENT DOCUMENTS

| | | | |
|---|---|---|---|
| 4,179,474 A * | 12/1979 | Beuther ................. | C10G 65/12 208/57 |
| 4,567,029 A | 1/1986 | Wilson et al. | |
| 5,484,755 A | 1/1996 | Lopez | |
| 6,403,854 B1 * | 6/2002 | Miller .................... | B01D 3/143 585/638 |
| 6,870,072 B2 * | 3/2005 | Lumgair ................... | C07C 1/20 208/161 |
| 7,329,790 B2 | 2/2008 | Bjorklund et al. | |
| 2004/0152939 A1 | 8/2004 | Pettigrew et al. | |
| 2004/0267069 A1 | 12/2004 | Ding et al. | |
| 2004/0267075 A1 | 12/2004 | Lumgair et al. | |
| 2005/0038304 A1 * | 2/2005 | Van Egmond ............ | C07C 1/20 585/324 |
| 2007/0103380 A1 | 5/2007 | Weste | |
| 2007/0155999 A1 | 7/2007 | Pujado et al. | |
| 2008/0161616 A1 | 7/2008 | Miller | |
| 2009/0048475 A1 | 2/2009 | Powers | |

FOREIGN PATENT DOCUMENTS

| | | |
|---|---|---|
| CN | 1055380 | 10/1991 |
| CN | 1809519 A | 7/2006 |
| CN | 101874007 | 10/2010 |
| CN | 101903311 | 12/2010 |
| WO | 0200579 A1 | 1/2002 |
| WO | 03037834 A1 | 5/2003 |
| WO | 03104170 A1 | 12/2003 |
| WO | 2006020083 | 2/2006 |
| WO | 2009045186 | 4/2009 |
| WO | 2009085565 | 7/2009 |

* cited by examiner

Primary Examiner — Sharon Pregler

(57) ABSTRACT

The invention provides a process for the preparation of an olefinic product, comprising:
(a) reacting an oxygenate feedstock, in a reaction zone in the presence of a molecular sieve catalyst, at a temperature from 350 to 1000° C., to produce a reaction effluent stream, comprising at least oxygenate, olefin, water and acidic by-products;
(b) cooling the reaction effluent stream by means of an indirect heat exchange to a temperature greater than the dew point temperature of reaction effluent stream;
(c) further rapidly cooling the reaction effluent stream to a temperature lower than the dew point temperature of the reaction effluent stream by direct injection of an aqueous liquid into the reaction effluent stream, to form a first quench effluent stream; and
(d) separating the first quench effluent stream into a first liquid quench effluent stream and a first gaseous quench effluent stream, comprising the olefinic product.

10 Claims, 6 Drawing Sheets

PROCESSES FOR THE PREPARATION OF AN OLEFINIC PRODUCT

PRIORITY CLAIM

The present application is the National Stage (§371) of International Application No. PCT/EP2013/072627, filed Oct. 29, 2013, which claims priority from European Patent Application No. 12190907.1, filed Oct. 31, 2012, incorporated herein by reference.

FIELD OF THE INVENTION

The present invention relates to a process for the preparation of an olefinic product, such as one or both of ethylene and propylene, from an oxygenate feedstock.

BACKGROUND OF THE INVENTION

Conventionally, ethylene and propylene are produced via steam cracking of paraffinic feedstocks comprising ethane or ethane/propane mixtures, known as gas cracking, or propane, butane, naphtha, NGL (natural gas liquids), condensates, kero, gas oil and hydrowax, known as naphtha cracking. An alternative route to ethylene and propylene an oxygenate-to-olefin (OTO) process. Interest in OTO processes for producing ethylene and propylene is growing in view of the increasing availability of natural gas. Methane in the natural gas can be converted into, for instance, methanol or dimethylether (DME), both of which are suitable feedstocks for an OTO process.

In an OTO process, an oxygenate such as methanol or dimethylether is provided to a reaction zone of a reactor comprising a suitable conversion catalyst and is converted to ethylene and propylene. In addition to the desired ethylene and propylene, a substantial part of the oxygenate such as methanol is converted to higher hydrocarbons including C4+ olefins, paraffins and carbonaceous deposits on the catalyst. The catalyst is continuously regenerated to remove a portion of the carbonaceous deposits by methods known in the art, for example heating the catalyst with an oxygen-containing gas such as air or oxygen.

The effluent from the reactor, comprising the olefins, any unreacted oxygenates such as methanol and dimethylether and other reaction products such as water, once separated from the bulk of the catalyst, may then be treated to provide separate component streams. In order to increase the ethylene and propylene yield of the process, the C4+ olefins component stream may be recycled to the reaction zone or alternatively further cracked in a dedicated olefin cracking zone to produce further ethylene and propylene.

Following reaction, the reaction effluent stream must be cooled before being treated to provide separate component streams. Conventionally, the reaction effluent stream is cooled to around 140 to 350° C. using one or more heat exchangers, often one or more transfer line exchangers (TLEs), before being contacted with a cooled aqueous stream in a quench tower. A quench tower comprises at least one set of internals such as packing and/or trays. In usual operation, the gaseous stream to be quenched is fed into the quench tower below the internals and one or more cooled aqueous stream is fed into the quench tower above the internals. Thus, the gaseous stream travels upwards through the quench tower and is brought into contact with the one or more cooled aqueous stream travelling downwards through the tower (counter-currently to the gaseous stream). An aqueous stream containing condensed materials is removed at the bottom of the tower, cooled and recycled. The cooled gaseous stream is removed from the top of the quench tower.

Catalyst fines are usually present in the reaction effluent stream, even after separation of the bulk of the catalyst. With continuous recycling of the aqueous streams (into which the catalyst fines will pass), any catalyst fines present in the reaction effluent stream build up on the internals, causing blockages. The complicated design of a quench tower also requires high capital expenditure (CAPEX).

Acidic by-products, such as formic acid and acetic acid, are formed in the reaction zone and are present in the reaction effluent stream. This formation of acidic by-products also continues as the reaction effluent stream is cooled to around 200° C. in one or more heat exchangers. As the gaseous reaction effluent stream is then further cooled, the components begin to condense to form liquids. The first drops of liquid formed are highly acidic (pH as low as 1 or 2), due to the presence of the acidic by-products. Such low pH material leads to corrosion of the process equipment. This corrosion is known as 'dew point corrosion' as it occurs at the dew point, which is the temperature at which a vapour in a volume of gas will condense into liquid, for a certain pressure.

When the reaction effluent stream is cooled in such a way that droplets of aqueous liquid form, concentrated dispersions of catalyst fines form within the liquid droplets. These form 'cakes' which may then be deposited on tubes and internals (for example, the quench tower internals) exacerbating the problems with fouling and blockages.

Due to the high temperatures in the reaction zone and the acidity of the catalyst, a portion of the oxygenates such as methanol may unavoidably decompose thermally or catalytically into oxides of carbon, i.e. carbon monoxide and carbon dioxide in the gaseous form.

Carbon dioxide generated during the OTO process is an acidic gas which is, thus, present in the effluent from the reactor. In order to prevent contamination of the olefinic product and problems associated with the formation of solid carbon dioxide during the separation of the olefinic product into olefinic component streams, which may be carried out at cryogenic temperatures, carbon dioxide should be removed from the reaction effluent and from the gaseous effluent from the cooling process before separation into olefinic component streams, for instance by treating with a caustic solution.

Carbonyl compounds, such as aldehydes and ketones, particularly formaldehyde and acetaldehyde, are commonly generated by the catalyst in side reactions and are thus found in the effluent from the reactor. High CO concentrations and long residence times at temperatures in the range of from 100 to 350° C., particularly in the presence of metal surfaces, will further promote the formation and accumulation of aldehydes. These carbonyl compounds may absorb and build up in the caustic solution used to remove carbon dioxide and other acid gases downstream of the quench section. The basic components of the caustic solution, such as hydroxide ions, can catalyse the aldol condensation and subsequent dehydration reactions of particularly acetaldehyde to form unsaturated aldehydes such as acrolein, especially at higher pH, such as a pH of greater than 9. Unsaturated aldehydes will polymerise when allowed to accumulate in the caustic solution and, if the aldol condensation reaction is left unchecked, viscous oily polymers and polymer films and lumbs can be formed. These are known as 'red oil', are insoluble in the caustic solution and can deposit on equipment internals, causing severe fouling and blockages.

It would be desirable to avoid the problems of dew point corrosion, catalyst fine fouling and red oil make in a process for the preparation of olefinic products from oxygenates. It would be highly desirable to achieve this without the fouling issues and high CAPEX associated with a quench tower.

SUMMARY OF THE INVENTION

Accordingly, the present invention provides a process for the preparation of an olefinic product, the process comprising the steps of:
(a) reacting an oxygenate feedstock, comprising oxygenate, in an oxygenate reaction zone in the presence of a catalyst comprising a molecular sieve, at a temperature in the range of from 350 to 1000° C., to produce a reaction effluent stream, comprising at least oxygenate, olefin, water and acidic by-products;
(b) cooling the reaction effluent stream by means of an indirect heat exchange to a temperature greater than the dew point temperature of reaction effluent stream;
(c) further rapidly cooling the reaction effluent stream to a temperature lower than the dew point temperature of the reaction effluent stream by direct injection of an aqueous liquid into the reaction effluent stream, to form a first quench effluent stream; and
(d) separating the first quench effluent stream into a first liquid quench effluent stream and a first gaseous quench effluent stream, comprising the olefinic product.

DETAILED DESCRIPTION OF THE INVENTION

Figure 1:
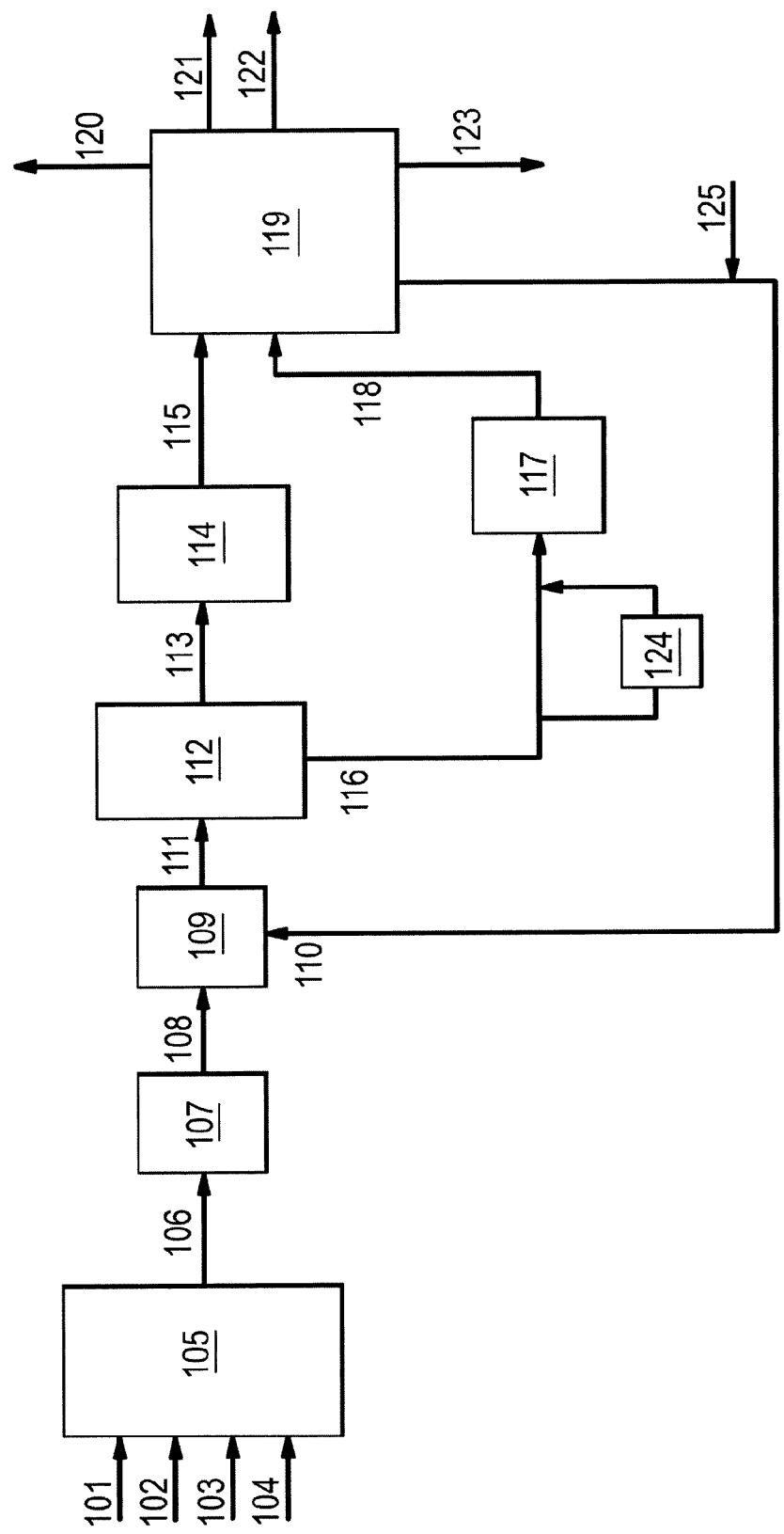
FIGS. 1 to 5 are schematic diagrams of exemplary, but non-limiting, embodiments of a process for the preparation of an olefinic product as described herein.

The present invention addresses the problems indicated by subjecting the reaction effluent stream to a direct quench with an aqueous liquid after initial indirect cooling in one or more heat exchangers. The direct quench rapidly cools the reaction effluent stream in the presence of a large quantity of water, thus preventing the formation of highly acidic droplets. As condensation of small droplets is avoided, the formation of catalyst fine cakes is also avoided. The rapid cooling also cuts down residence time at temperatures which encourage aldehyde make and, therefore, prevents further aldehyde formation at this stage of the process and reduces red oil make in the basic environment of a caustic wash tower downstream of the quench section.

Since the solids-containing liquid phase is removed from the process, the downstream conduits and equipment can be designed more freely as there is not a solids issue to deal with. For example, the conduit between the direct quench step and any further equipment can have a lower velocity or be directed in an upward direction if desired without concern for solids or fouling.

In addition, since a large part of the cooling is carried out in the direct quench step, less cooling is required in downstream equipment. Further, since the temperature is lower, the gas volume is reduced and the downstream equipment can be smaller. Another benefit is that the direct quench system can be designed for a very high turndown which is much higher than for a heat exchanger or quench tower.

In step (b) the reaction effluent stream is cooled by means of an indirect heat exchange to recover the heat contained in the reactor effluent. Typically, the reaction effluent stream is indirectly contacted with a liquid stream, which is at a lower temperature, in a heat exchanger. The liquid stream is suitably a process stream, for instance a reactor feed, or a water stream. The heat exchanger may be of any type known in the art, for instance a transfer line exchanger (TLE) and/or a feed/effluent exchanger. Preferably, a shell and tube type heat exchanger is used.

In step (b) the reaction effluent stream is cooled to a temperature greater than the dew point of the reaction effluent stream. Preferably the reaction effluent stream is cooled to a temperature of no less that 140° C., more preferably no less than 150° C., most preferably no less than 160° C. Preferably, the reaction effluent stream is cooled in step (b) to a temperature of at most 370° C., more preferably at most 320° C., more preferably at most 270° C., more preferably at most 250° C., even more preferably at most 240° C., even more preferably at most 220° C., even more preferably at most 200° C., even more preferably at most 190° C., most preferably at most 180° C.

The reaction effluent stream is further cooled in step (c) by injection of an aqueous liquid directly into the reaction effluent stream. The aqueous liquid is preferably water. It may suitably be fresh water, but preferably is a recycled stream from a later stage of the process for the preparation of an olefinic product.

Suitably, the aqueous liquid is at a temperature of at least 10° C., preferably at least 20° C., more preferably at least 25° C. Suitably the aqueous liquid is at a temp of at most 65° C., preferably at most 40° C., more preferably at most 35° C.

The term 'direct injection' as used herein, indicates that the aqueous liquid is provided straight into the reaction effluent stream by a quench fitting suitable for dispersing the water into fine droplets, effectively forcing the liquid as fine droplets into the gas stream. The injection of the aqueous stream is co-current to the direction of flow of the reaction effluent stream.

The aqueous liquid is injected into the reaction effluent stream by means of a quench fitting. The quench fitting may be any means known in the art capable of rapidly introducing a large quantity of water directly into a gaseous stream, but suitably comprises a spray nozzle.

In one embodiment, the quench fitting comprises aqueous liquid injection facilities wherein the aqueous liquid is injected directly into a pipe or other conduit transporting the reaction effluent stream from the reactor and/or heat exchangers downstream of the reactor.

In one embodiment, spray nozzles are located in the sides of the conduit such that the aqueous liquid is injected directly into the conduit transporting the reaction effluent stream.

The aqueous stream is injected into the reaction effluent stream such that the mass ratio of the aqueous stream to be injected to the total contents of the reaction effluent stream is preferably at least 3:1, more preferably at least 4:1, most preferably at least 5:1. Preferably, the mass ratio of the aqueous stream to be injected to the total contents of the reaction effluent stream is at most 20:1, more preferably at most 15:1, even more preferably at most 10:1, most preferably at most 8:1.

After cooling in step (c) the first quench effluent stream must be at a temperature below the dew point temperature of the reaction effluent stream. Preferably the first quench effluent stream is at a temperature of no more than 100° C., more preferably less than 100° C., more preferably no more than 95° C., most preferably no more than 90° C., most preferably no more than 85° C. Preferably, the first quench effluent stream is at a temperature of at least 30° C., more preferably at least 40° C., more preferably at least 50° C., even more preferably at least 60° C., even more preferably at least 65° C., even more preferably at least 70° C., even more preferably at least 80° C., most preferable at least 85° C.

After cooling in step (c), the first quench effluent stream is separated into a first liquid quench effluent stream and a first gaseous quench effluent stream. The separation may occur in any suitable separation apparatus known in the art. In one preferred embodiment, a knock out drum is used for separation. An added advantage of the present invention is that apparatus, such as a knock out drum, without any internals can be used, further reducing the possibility of fouling. The first gaseous quench effluent stream comprises the olefinic product and any other material present in gaseous form at the temperature of the first quench effluent stream.

The first liquid quench effluent stream comprises at least water, oxygenates, solids and liquid hydrocarbons.

The first gaseous quench effluent stream is then subjected to further cooling, for example in an air or cooling water cooler, and condensed material is removed, before it is subjected to purification and separation to the desired products.

The first aqueous quench effluent stream may also be cooled further and separated to form an aqueous oxygenate stream, a liquid hydrocarbons stream, a solids (slurry) stream and an aqueous stream, which may be recycled, optionally cooled and used for direct injection in step (c).

Reference herein to an oxygenate feedstock is to an oxygenate-comprising feedstock. In the oxygenate (or OTO) reaction zone, at least part of the feedstock is converted into a product containing one or more olefins, preferably including lower olefins, in particular ethylene and typically propylene.

The oxygenate used in the process is preferably an oxygenate which comprises at least one oxygen-bonded alkyl group. The alkyl group preferably is a C1-C5 alkyl group, more preferably C1-C4 alkyl group, i.e. comprises 1 to 5 or 1 to 4 carbon atoms respectively; more preferably the alkyl group comprises 1 or 2 carbon atoms and most preferably one carbon atom. Examples of oxygenates that can be used in the oxygenate feedstock include alcohols and ethers. Examples of preferred oxygenates include alcohols, such as methanol, ethanol, propanol; and dialkyl ethers, such as dimethyl ether, diethyl ether, methylethyl ether. Preferably, the oxygenate is methanol or dimethyl ether, or a mixture thereof.

Preferably, the oxygenate feedstock comprises at least 50 wt % of oxygenate, in particular methanol and/or dimethyl ether, based on total hydrocarbons, more preferably at least 70 wt %.

An oxygenate co-feed, comprising oxygenate recovered or produced in the process downstream of step (d) of the process of the present invention, such as an oxygenate recovered stream, may also be supplied, as discussed below. Such a stream may contain methanol, dimethyl ether and/or MTBE.

A diluent, such as water or steam, may also be provided to the oxygenate reaction zone. The molar ratio of oxygenate to diluent may be between 10:1 and 1:10, preferably between 4:1 and 1:2, in particular when the oxygenate is methanol and the diluent is water (typically steam).

Preferably, in addition to the oxygenate and diluent, an olefinic co-feed is provided along with and/or as part of the oxygenate feedstock. Reference herein to an olefinic co-feed is to an olefin-comprising co-feed.

The olefinic co-feed preferably comprises C4+ olefins i.e. C4 and higher olefins, more preferably C4 and C5 olefins.

In one preferred embodiment of the present invention, the olefinic co-feed comprises at least 30 wt %, preferably at least 50 wt %, more preferably at least 70 wt % of C4 hydrocarbon species. In this embodiment, the remainder of the olefinic co-feed comprises at least 70 wt %, more preferably at least 80 wt %, even more preferably at least 90 wt % C5 hydrocarbon species.

In a second preferred embodiment of the present invention, the olefinic co-feed comprises at least 50 wt %, preferably at least 70 wt % of C5 hydrocarbon species. In this embodiment, the remainder of the olefinic co-feed comprises at least 70 wt %, more preferably at least 80 wt %, even more preferably at least 90 wt % C4 hydrocarbon species.

Of the C4 hydrocarbon species present in the olefinic co-feed, preferably at least 35 wt %, more preferably at least 50 wt %, more preferably at least 75 wt % are olefins.

Of the C5 hydrocarbon species present in the olefinic co-feed, preferably at least 30 wt %, more preferably at least 45 wt % are non-cyclic olefins.

In order to maximize production of ethylene and propylene, it is desirable to maximize the recycle of C4 olefins in the effluent of the OTO process. This can be done by recycling at least part of the C4+ hydrocarbon fraction, preferably C4-C5 hydrocarbon fraction, more preferably C4 hydrocarbon fraction, in the OTO effluent. However, a certain part thereof, such as between 1 and 5 wt %, can be withdrawn as purge, since otherwise saturated hydrocarbons, in particular C4s (normal and iso butane) may build up in the process, which are substantially not converted under the OTO reaction conditions. Preferably, at least 70 wt % of the olefinic co-feed, during normal operation, is formed by a recycle stream of a C4+ hydrocarbon fraction from the OTO reaction effluent. Preferably, at least 90 wt % of olefinic co-feed, based on the whole olefinic co-feed, is formed by such recycle stream.

The preferred molar ratio of oxygenate in the oxygenate feedstock to olefin in the olefinic co-feed provided to the oxygenate reaction zone depends on the specific oxygenate used and the number of reactive oxygen-bonded alkyl groups therein. Preferably the molar ratio of oxygenate to olefin in the total feed lies in the range of 20:1 to 1:10, more preferably in the range of 18:1 to 1:5, still more preferably in the range of 15:1 to 1:3, even still more preferably in the range of 12:1 to 1:3.

A variety of OTO processes are known for converting oxygenates, such as for instance methanol or dimethyl ether to an olefin-containing product, as already referred to above. One such process is described in WO 2006/020083. Processes integrating the production of oxygenates from synthesis gas and their conversion to light olefins are described in US 20070203380 and US 20070155999.

Catalysts suitable for converting the oxygenate feedstock comprise molecular sieve. Such molecular sieve-comprising catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing tetrahedral units, more preferably, two or more [SiO$_4$], [AlO$_4$] and/or [PO$_4$] tetrahedral units. These silicon, aluminum and/or phosphorus based molecular sieves and metal containing silicon, aluminum and/or phosphorus based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å.

Suitable molecular sieves are silicoaluminophosphates (SAPO), such as SAPO-17, -18, 34, -35, -44, but also SAPO-5, -8, -11, -20, -31, -36, 37, -40, -41, -42, -47 and -56; aluminophosphates (AlPO) and metal substituted (silico) aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanides of the Periodic Table of Elements. Preferably, the substituted metal atom (Me) is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, and the FER type. Other suitable zeolites are for example zeolites of the STF-type, such as SSZ-35, the SFF type, such as SSZ-44 and the EU-2 type, such as ZSM-48.

Aluminosilicate-comprising catalyst, and in particular zeolite-comprising catalyst are preferred when an olefinic co-feed is fed to the oxygenate conversion zone together with oxygenate, for increased production of ethylene and propylene.

Preferred catalysts comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably, the channels in at least one of the directions are 10-membered ring channels. A preferred MFI-type zeolite has a silica-to-alumina ratio, SAR, of at least 60, preferably at least 80. More preferred MFI-type zeolites have a silica-to-alumina ratio in the range of from 60 to 150, more preferably of from 80 to 100, Particular catalysts include catalysts comprising one or more zeolites having one-dimensional 10-membered ring channels, i.e. one-dimensional 10-membered ring Channels, which are not intersected by other channels. Preferred examples are zeolites of the MTT and/or TON type. Preferably, the catalyst comprises at least 40 wt %, preferably at least 50 wt %. of such zeolites based on total zeolites in the catalyst. In one embodiment, the catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst may further comprise phosphorus as such or in a compound, i.e. phosphorus other than any phosphorus included in the framework of the molecular sieve. It is preferred that a MEL or MFI-type zeolite comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorus as such or in a compound in an elemental amount of from 0.05 to 10 wt % based on the weight of the formulated catalyst. A particularly preferred catalyst comprises phosphorus and MEL or MFI-type zeolite having SAR of in the range of from 60 to 150, more preferably of from 80 to 100. An even more particularly preferred catalyst comprises phosphorus and ZSM-5 having SAR of in the range of from 60 to 150, more preferably of from 80 to 100.

It is preferred that molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. It is well known in the art how to produce such molecular sieves in the hydrogen form.

The reaction conditions of the oxygenate conversion, include a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Preferably, the oxygenate feedstock is preheated to a temperature in the range of from 200 to 550° C., more preferably 250 to 500° C. prior to contacting with the molecular sieve-comprising catalyst.

The catalyst particles used in the process can have any shape known to the skilled person to be suitable for this purpose, and can be present in the form of spray dried catalyst particles, spheres, tablets, rings, extrudates, etc. Extruded catalysts can be applied in various shapes, such as, cylinders and trilobes. Spray-dried particles allowing use in a fluidized bed or riser reactor system are preferred. Spherical particles are normally obtained by spray drying. Preferably the average particle size is in the range of 1-200 µm, preferably 50-100 µm.

Although the C4+ hydrocarbon fraction in the reaction effluent may be recycled as an olefinic co-feed as discussed above, in an alternative embodiment, at least part of the olefins in the C4+ hydrocarbon fraction are converted to ethylene and/or propylene by contacting the C4+ hydrocarbon fraction in a separate unit with a molecular sieve-comprising catalyst, particularly a zeolite-comprising catalyst. This is particularly preferred where molecular sieve-comprising catalyst in the OTO process comprises a least one SAPO, AlPO, or MeAlPO type molecular sieve, preferably SAPO-34. These catalysts are less suitable for converting C4+ olefins. Preferably, the C4+ hydrocarbon fraction is contacted with the zeolite-comprising catalyst at a reaction temperature of 350 to 1000° C., preferably from 375 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Optionally, the stream comprising C4+ olefins also contains a diluent. Examples of suitable diluents include, but are not limited to, liquid water or steam, nitrogen, argon, paraffins and methane. Under these conditions, at least part of the olefins in the C4+ hydrocarbon fraction are converted to further ethylene and/or propylene. The further ethylene and/or propylene may be combined with the further ethylene and/or propylene obtained directly from the oxygenate reaction zone. Such a separate process step directed at converting C4+ olefins to ethylene and propylene is also referred to as an olefin cracking process (OCP).

Catalysts comprising molecular sieve, particularly aluminosilicate-comprising catalysts, and more particularly zeolite-comprising catalysts, have the further advantage that in addition to the conversion of methanol or ethanol, these catalysts also induce the conversion of olefins to ethylene and/or propylene. Therefore, aluminosilicate-comprising catalysts, and in particular zeolite-comprising catalysts, are particularly suitable for use as the catalyst in an OCP. Particular preferred catalysts for the OCP reaction, i.e. converting part of the olefinic product, and preferably part of the C4+ hydrocarbon fraction of the olefinic product including C4+ olefins, are catalysts comprising at least one zeolite selected from MFI, MEL, TON and MTT type zeolites, more preferably at least one of ZSM-5, ZSM-11, ZSM-22 and ZSM-23 zeolites.

Both the OTO process and the OCP may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

The catalyst can deactivate in the course of the OCP and OTO process. The deactivation occurs primarily due to deposition of carbonaceous deposits, such as coke, on the catalyst by side reactions. The deactivated catalyst can be regenerated to remove a portion of the carbonaceous deposit by methods known in the art. It is not necessary, and indeed may be undesirable, to remove all the carbonaceous deposit from the catalyst as it is believed that a small amount of residual carbonaceous deposit such as coke may enhance the catalyst performance. Additionally, it is believed that complete removal of the carbonaceous deposit may also lead to degradation of the molecular sieve.

The same catalyst may be used for both the OTO process and OCP. In such a situation, the catalyst comprising molecular sieve, particularly comprising aluminosilicate molecular sieve and more particularly comprising zeolite, may be first used in the OCP reaction zone for the conversion of the C4+ olefins of the C4+ hydrocarbon fraction. The catalyst from the OCP may then be used, typically without regeneration, in the OTO process for conversion of an oxygenate feedstock and an olefinic co-feed. The deactivated catalyst from the OTO process may then be regenerated as described herein, and the regenerated catalyst then used again in the OCP.

This line-up may be beneficial because it provides good heat integration between the OCP, OTO and regeneration processes. The OCP is endothermic and at least a portion of the heat of reaction can be provided by passing catalyst from the regeneration zone to the OCP reaction zone, because the regeneration reaction which oxidizes the carbonaceous deposits from the loaded catalyst is exothermic.

Embodiments of the present invention will now be described by way of example only and with reference to the accompanying non-limiting figures.

FIG. 1 exemplifies an embodiment of the present invention. An oxygenate feedstock 101 is fed into the oxygenate reaction zone 105. An oxygenate co-feed 102 may also be supplied by an oxygenate recycle stream. A diluent 103 may also be provided to the reaction zone. Preferably, an olefinic co-feed 104 is also provide to the reaction zone. The oxygenate co-feed, diluent and olefinic co-feed may be supplied to the reaction zone separately or one or more of these streams may be combined with the oxygenate feedstock or together before being fed to the reaction zone.

In the oxygenate (or OTO) reaction zone 105, reaction is carried out in the presence of a catalyst at a temperature in the range of from 350 to 1000° C. Following reaction, the gaseous product is separated from the bulk of the catalyst to produce a reaction effluent stream 106. The reaction effluent stream is cooled in one or more heat exchangers 107 situated in series, to provide a cooled reaction effluent stream 108 at a temperature greater than the dew point temperature of the reaction effluent stream and preferably in the range of from 150 to 250° C. An aqueous liquid 110 is directly injected into the cooled reaction effluent stream through a quench fitting (e.g. a spray nozzle) 109, rapidly cooling said stream by mixing it with a large quantity of water to a temperature below the dew point temperature of the reaction effluent stream.

The resultant first quench effluent stream 111 is preferably at a temperature in the range of from 60 to 95° C. and is separated in separator 112 (suitably a knock out drum) to provide a first gaseous quench effluent stream 113 and a first liquid quench effluent stream 116. Further cooling of each stream may be provided by air or water coolers 114 and 117, respectively.

In an optional embodiment of the present invention, all or part of the first liquid quench effluent stream 116 may be used to provide heat to a further part of the process 124, for instance a propane/propylene splitter, thus providing enhance heat integration of the overall process.

Further cooled gaseous 115 and liquid 118 streams are then fed to a decanter or settler 119 for separation. It should be noted at this stage that the gaseous stream 115 may contain some liquid (condensed) material. Typically, the streams at this stage are at a temperature in the range of from 20 to 50° C. An olefin rich gas stream 120 is produced. An aqueous liquid 110 is recycled. A solid stream 123, usually in the form of a slurry, is produced and the catalyst solids therein can be re-used. An oxygenate containing aqueous stream 121 can be subjected to further separation and purification before recycling of the thus-formed oxygenate recovered stream to the oxygenate reaction zone. Liquid hydrocarbon stream 122 may be separated as a waste stream or for use as fuel.

A basic material, for instance a caustic solution, 125 may be added into the process to prevent the lowering of the pH due to the accumulation of acids in the recycle streams.

Figure 2:
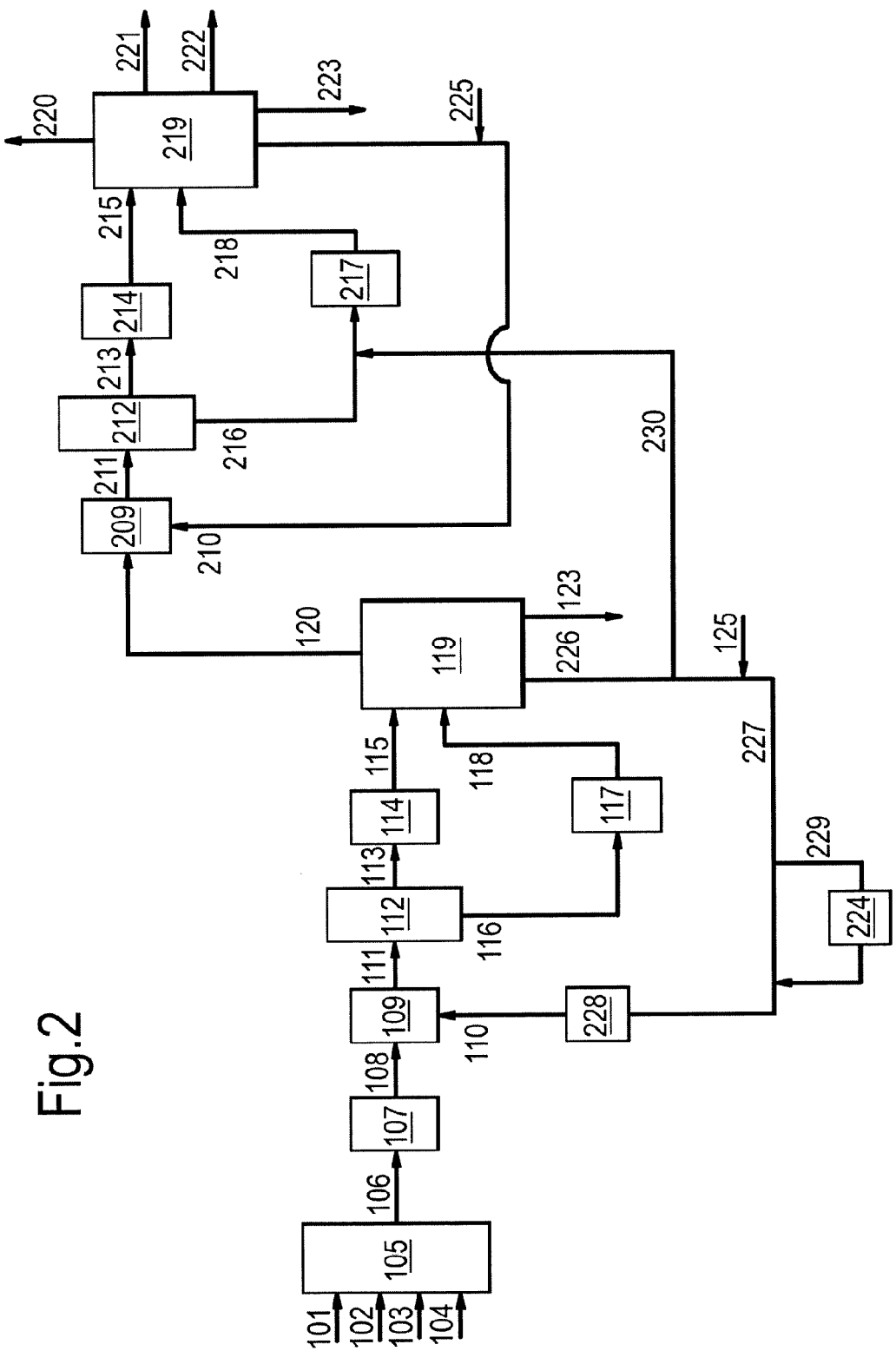

FIG. 2 shows an embodiment of the invention wherein the cooling and separation processes are carried out in two stages.

The first stage of the process is carried out in a similar manner as in the embodiment shown in FIG. 1. However, less cooling is applied or the reaction effluent stream starts at a higher temperature, so that the temperature of the gas and liquid streams in separator 119, though below the dew point temperature of the reaction effluent stream, is still in the range of from 50 to 95° C., preferably in the range of from 60 to 90° C.

In this embodiment, the streams from the separator include an olefin rich gas stream 120, a solid stream 123 and a combined aqueous stream 226. The combined aqueous stream is split to form an aqueous recycle stream 227 and a surplus aqueous material and hydrocarbons stream 230. The aqueous recycle stream is then treated in a heat exchanger 228 to cool it to a suitable temperature for use as the aqueous liquid 110 used for direct injection. An added advantage of this embodiment is that the aqueous recycle stream is at a suitable temperature such that all or part 229 of it may be used to provide heat to a further part of the process 224, thus providing enhanced heat integration for the overall process.

The olefin rich gas stream 120 in this embodiment is provided to quench nozzle 209 and an aqueous liquid 210 is directly injected into the stream in order to provide further cooling. The resultant second quench effluent stream 211 is separated in separator 212 (suitably a knock out drum) to provide a second gaseous quench effluent stream 213 and a second liquid quench effluent stream 216. Further cooling of each stream may be provided by air or water coolers 214 and 217 respectively.

The resultant gaseous 215 (which may at this stage contain some liquid due to further condensation at a lower temperature) and liquid 218 streams are then fed to a decanter or settler for separation. The material in the decanter or settler is typically at a temperature in the range of from 20 to 50° C., preferably in the range of from 20 to 40° C.

A second olefin rich gas stream 220 is produced. An aqueous liquid 210 is recycled. A solid stream 223, usually in the form of a slurry is produced and the catalyst solids therein can be re-used. An oxygenate containing stream 221 can be subjected to further separation and purification before recycling of the thus-formed oxygenate recovered stream to the oxygenate reaction zone as at least part of the oxygenate co-feed 102. Liquid hydrocarbon stream 222 may be separated as a waste stream or for use as fuel.

Surplus aqueous material and liquid hydrocarbons stream 230 from the first stage direct quench can be added to the second liquid quench stream 216.

A basic material, for instance a caustic solution, may be added at one or more points 125, 225 to prevent the lowering of the pH due to the accumulation of acids in the recycle streams.

Figure 3:
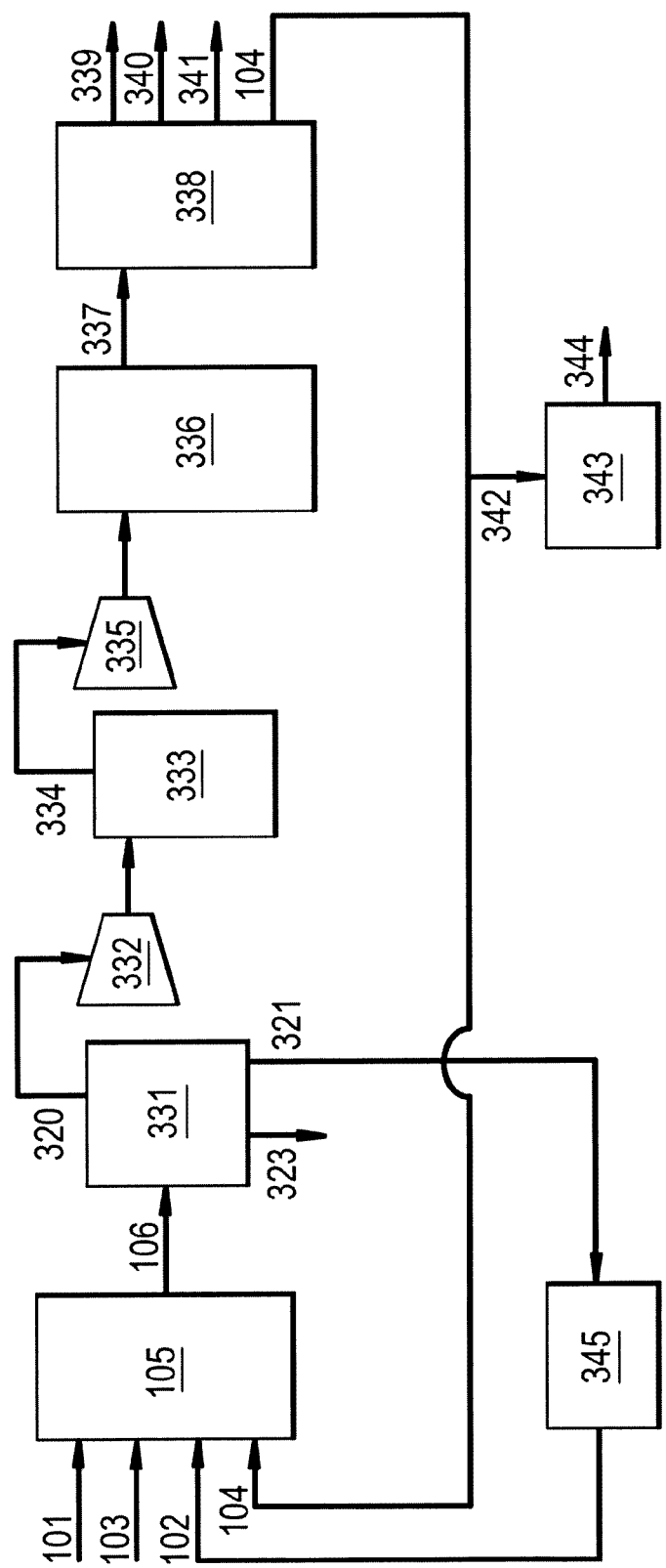

FIG. 3 shows one possible embodiment of the invention as it is incorporated into an overall process for the production of olefinic products such as ethylene and propylene. Oxygenate feedstock 101, an oxygenate co-feed 102, a diluent 103 and an olefinic co-feed 104 are provided to an oxygenate reaction zone 105. Reaction is carried out in the presence of a catalyst at elevated temperatures. The reaction product is separated from the catalyst to provide reaction effluent stream 106. The cooling and initial separation steps (b), (c) and (d) of the present invention are carried out one or more times in series or in parallel to provide an olefin rich gas stream 320. An oxygenate containing aqueous stream 321 is also produced and can be subjected to separation and purification in the oxygenate separation zone 345 before being recycled as the oxygenate co-feed 102. A solid stream 323 is also produced.

The olefin rich gas stream 320 is compressed in one or more gas compressors 332, each compressor comprising one or more compressor stages, and is then passed to a carbonyl compound absorption zone 333 in which the stream is treated with a caustic solution to remove carbon dioxide and carbonyl compounds. The resultant stream 334 is further compressed in one or more compressors 335 before being passed to water removal zone 336. After water removal, the remaining gas stream enters an olefin separation zone 338 to be separated, preferably by one or more cryogenic distillation processes, to provide two or more olefinic component streams 339, 340, 341 and 104, including a stream comprising C4+ olefins which is recycled as olefinic co-feed 104.

In one alternative embodiment, all or part 342 of this stream is subjected to an OCP 343 to provide a stream comprising ethylene and propylene 344. This stream 344 can then be fed back into the process as part of olefin rich gas stream 320.

Figure 4:
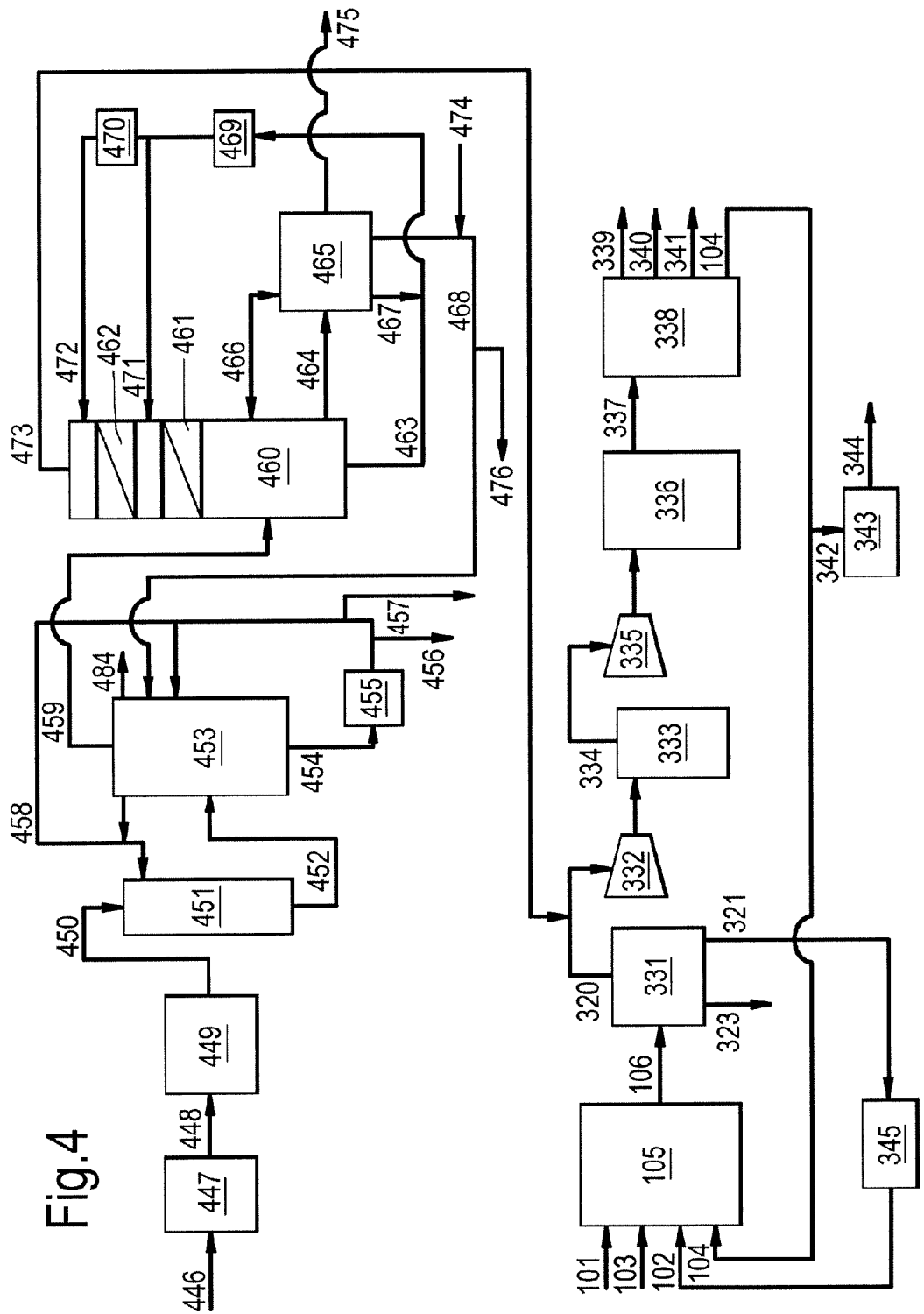

FIG. 4 shows an embodiment of the present invention wherein it is combined with a process for producing an olefinic product by naphtha cracking.

Feed stream 446, comprising any, preferably paraffinic, feedstocks within the boiling range of propane, butane, naphtha, NGL (natural gas liquid), condensate, kero, gas oil or hydrowax, is subjected to cracking in one or more parallel pyrolysis furnaces/reactors 447, by heating at a temperature in the range of from 750 to 900° C. The cracked effluent product stream is produced in a multitude of parallel coils in one pyrolysis furnace. The cracked effluent is cooled in one or more parallel transfer line exchangers per furnace. In FIG. 4, stream 448 represents all cracked effluent product streams of all furnaces. Each furnace has one or more transfer line exchanger in series 449, which cool the temperature down to a temperature in the range of from 300 to 650° C. The thus-cooled stream 450 is subjected to an oil quench via quench fitting 451 to further reduce the temperature to in the range of from 150 to 270° C. One or more streams 452 produced in this manner are then fed to a gasoline fractionator 453. A bottoms stream 454 of the gasoline fractionator is removed and passed through heat exchangers, before being recycled to the fractionator or used as the oil quench 458. Side product streams including ECR (ethylene cracked residue, being stripped using quench oil) 456, CGO (cracked gas oil) and solids/coke 457 can be removed from the bottoms stream. Optionally, a side stream CGO (cracked gas oil) 484 can be produced from the gasoline fractionator.

A gaseous stream 459 is removed from the top of the gasoline fractionators and fed to a quench tower 460, containing one or more sets of internals (461 and 462). An aqueous stream 463 is removed from the bottom of the quench tower and is recycled 471, 472 after cooling in heat exchangers 469, 470. A side draw 464 from the quench tower bottom compartment is fed to separation vessel 465 providing a gaseous stream 466, a recycle aqueous stream 467, a gasoline-containing stream 468, which is fed back into the gasoline fractionators 453, with a bleed 476, and a process water stream 475 for further processing. The olefin rich quench tower overhead stream 473 can be combined with the olefin rich gas stream 320 from the OTO process.

Figure 5:
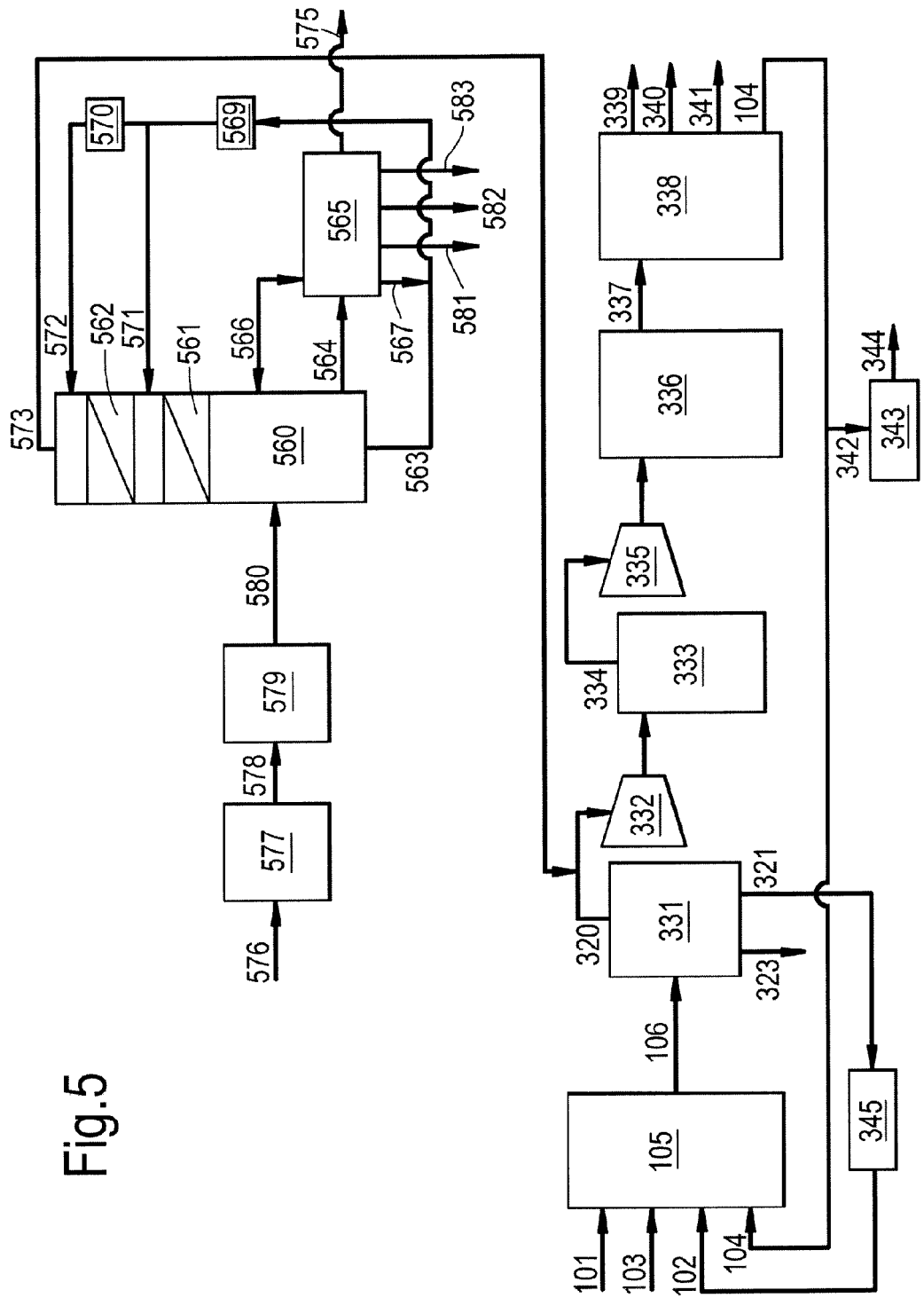

FIG. 5 shows an embodiment of the present invention wherein it is combined with a process for producing an olefinic product by ethane or ethane/propane cracking.

Ethane or ethane/propane feed 576 is provided to one or more parallel pyrolysis furnaces/reactors 577 and heated at temperatures in the range from of 800 to 950° C. Each pyrolysis furnace consists of a multitude of parallel coils producing cracked effluent. Each pyrolysis furnace has parallel transfer line exchangers. Each pyrolysis furnace can have one or more transfer line exchangers in series. The effluent gas stream 578 represents the furnace effluent of all pyrolysis furnaces. The furnace effluent from the pyrolysis furnaces/reactors is cooled to a temperature in the range of from 180 to 320° C. in one or more heat exchangers 579 in series. One or more gas streams 580 produced by this method are combined and fed to the bottom of a quench tower 560 containing one or more internals 561 and 562. The quench tower is operated as described for FIG. 4. In the separator 565, coke 581, heavy oil/pitch 582, pygas/gasoline 583 and process water stream 475 streams are separated for processing and/or use elsewhere.

It should be noted herein that, in the numbers on FIGS. 1-5 and referred to in the text, corresponding features on different Figures will have the same second and third digits in their indicative numbers, with the first digit referring to the Figure number. Thus, number 460 and 560 will refer to the same feature in FIGS. 4 and 5, respectively.

Figure 6A:
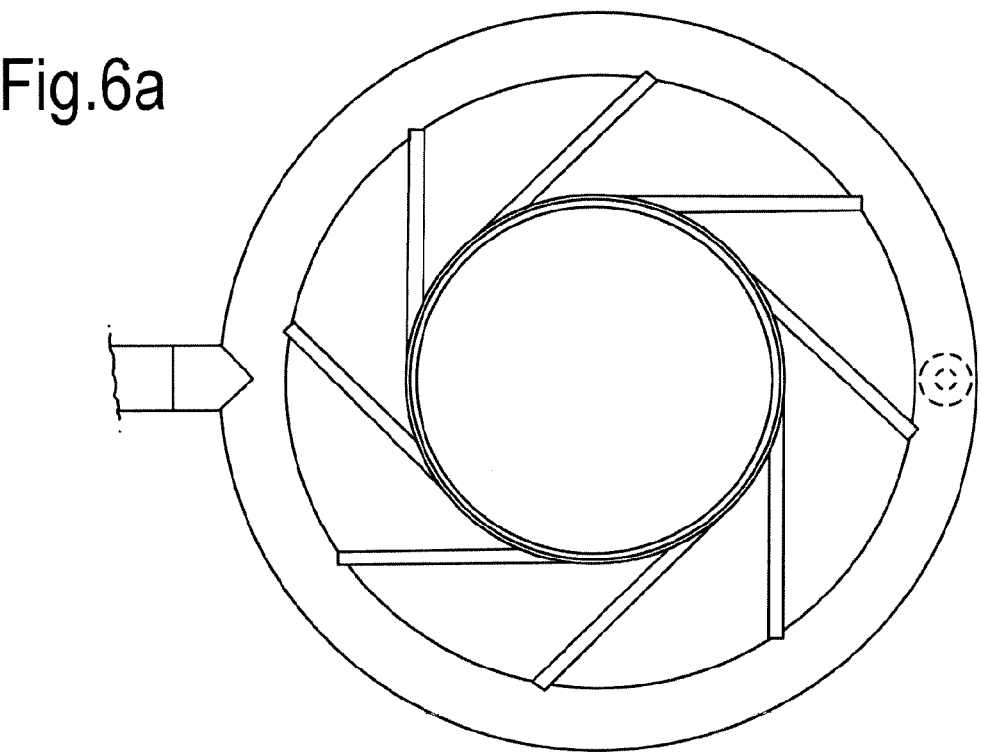
FIG. 6 provides 2 views (6A and 6B) of an embodiment of a quench fitting.
Figure 6B:
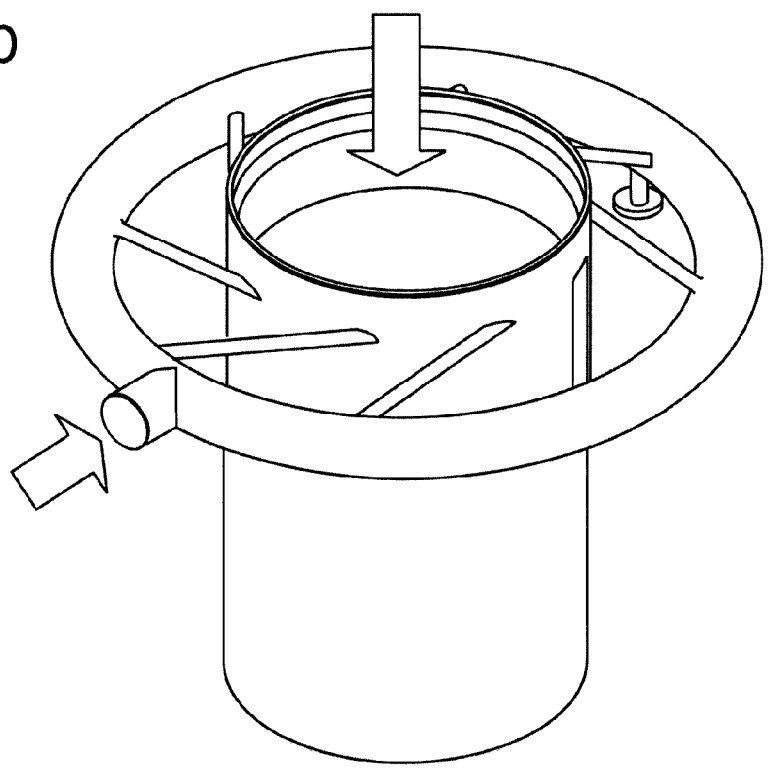

FIG. 6 uses a different numbering scheme than FIGS. 1-5 and the items in this Figure are not related by number to any of the previous Figures. FIG. 6 depicts an embodiment of a direct quench fitting with two views, 6A and 6B. FIG. 6A shows a top view of a direct quench fitting. The quench ring 610 is concentric to the effluent conduit 620 and the direct quench points 630 are located at a plurality of points around the effluent conduit. The direct quench points may be spray nozzles or another type of injection device for injecting the aqueous liquid into the effluent conduit FIG. 6B shows a side view of the quench ring 610, the effluent conduit 620 and the direct quench points 630.

That which is claimed is:

1. A process for the preparation of an olefinic product, the process comprising the steps of:
   (a) reacting an oxygenate feedstock, comprising oxygenate, in an oxygenate reaction zone in the presence of a catalyst comprising a molecular sieve, at a temperature in the range of from 350 to 1000° C., to produce a reaction effluent stream, comprising at least oxygenate, olefin, water and acidic by-products;
   (b) cooling the reaction effluent stream by means of an indirect heat exchange to a temperature greater than the dew point temperature of reaction effluent stream;
   (c) further rapidly cooling the heat exchanged reaction effluent stream to a temperature lower than the dew point temperature of the reaction effluent stream by direct injection of an aqueous liquid into a conduit transporting the reaction effluent stream from the heat exchange of step (b)
   (d) separating the first quench effluent stream into a first liquid quench effluent stream and a first gaseous quench effluent stream, comprising the olefinic product wherein in step (c) the aqueous liquid is injected by means of a quench fitting.

2. A process as claimed in claim 1, wherein in step (b) the reaction effluent stream is cooled to a temperature in the range of from 140° C. to 370° C.

3. A process according to claim 1, wherein the quench fitting comprises a spray nozzle.

4. A process according to claim 1, wherein in step (c) the heat exchanged reaction effluent stream is cooled such that the first quench effluent stream is at a temperature in the range of from 30 to 100° C.

5. A process according to claim 1, wherein in step (c) the heat exchanged reaction effluent stream is cooled such that the first quench effluent stream is at a temperature in the range of from 50 to 150° C.

6. A process according to claim 1, wherein the first gaseous quench effluent stream is subsequently subjected to further cooling and any further condensed materials are removed therefrom in order to provide an olefin rich gas stream.

7. A process for the preparation of an olefinic product, said process comprising preparing first gaseous quench effluent stream, comprising the olefinic product according to the process of claim 1 and combining it with a further olefin rich gas stream obtained from a cracking process to form a combined olefin rich gas stream.

8. A process according to claim 7, wherein the further olefin rich gas stream is obtained from a naphtha cracking process comprising the steps of:
   (a) heating a feed comprising a feedstock within the boiling range of propane, butane, naphtha, NGL, condensate, kero, gas oil or hydrowax at a temperature in the range of from 750 to 900° C. in a pyrolysis furnace to produce a naphtha furnace effluent stream;
   (b) cooling the naphtha furnace effluent stream by means of an indirect heat exchange to a temperature in the range of from 300 to 650° C.;
   (c) further rapidly cooling the naphtha furnace effluent stream to a temperature in the range of from 150 to 270° C. by direct injection of an oil into the naphtha furnace effluent stream to produce an oil-quenched effluent stream;
   (d) treating the oil quenched effluent stream in a fractionator to produce a fractionated gaseous stream; and
   subsequently contacting the fractionated gaseous stream with an aqueous stream in a quench section to produce the further olefin rich gas stream.

9. A process according to claim 7, wherein the further olefin rich gas stream is obtained from an ethane or ethane/propane cracking process comprising the steps of:
   (a) heating a feed comprising ethane and/or propane at a temperature in the range of from 800 to 950° C. in a pyrolysis furnace to produce a ethane furnace effluent stream;
   (b) cooling the ethane furnace effluent stream to a temperature in the range of from 180 to 320° C. in one or more heat exchangers in series; and
   (c) contacting the resultant ethane furnace effluent stream with an aqueous stream in a quench tower to produce the further olefin rich gas stream.

10. A process for the production of an olefinic product according to claim 7, wherein the combined olefin rich gas stream is purified and separated by a process comprising the steps of:
   (a) compressing the combined olefin rich gas stream;
   (b) treating the compressed stream with a caustic solution to absorb carbon dioxide and carbonyl compounds;
   (c) further compressing the stream produced in step (b);
   (d) removing water from the stream produced in step (c); and
   (e) separating the stream produced in step (d) into olefinic products by means of cryogenic distillation.

* * * * *